US007785600B2

(12) United States Patent
Tu et al.

(10) Patent No.: US 7,785,600 B2
(45) Date of Patent: Aug. 31, 2010

(54) COMPOSITIONS AND METHODS FOR TREATING ALLERGIES, AUTO-IMMUNE DISEASES, AND IMPROVING SKIN CONDITION BY GANODERMA LUCIDUM (REISHI) POLYSACCHARIDES

(75) Inventors: Tseng-Rong Tu, Taitung (TW); Chia-Feng Li, Caotun Township (TW); Sung-Hsieh Su, Taipei (TW); Chi-Huey Wong, La Jolla, CA (US); Eugene Fan, La Jolla, CA (US)

(73) Assignees: Wyntek Corporation, Taipei (TW); Academia Sinica, Taipei (TW)

( * ) Notice: Subject to any disclaimer, the term of this patent is extended or adjusted under 35 U.S.C. 154(b) by 4 days.

(21) Appl. No.: 12/201,879

(22) Filed: Aug. 29, 2008

(65) Prior Publication Data

US 2009/0060939 A1 Mar. 5, 2009

Related U.S. Application Data

(60) Provisional application No. 60/969,119, filed on Aug. 30, 2007.

(51) Int. Cl.
*A61K 36/06* (2006.01)
*A61K 9/00* (2006.01)
*A61K 47/00* (2006.01)

(52) U.S. Cl. ................... 424/195.15; 424/400; 424/439

(58) Field of Classification Search ........................ None
See application file for complete search history.

(56) References Cited

U.S. PATENT DOCUMENTS

| | | | |
|---|---|---|---|
| 4,522,811 | A | 6/1985 | Eppstein et al. |
| 5,334,704 | A | 8/1994 | Tsunoo et al. |
| 6,395,310 | B1 | 5/2002 | Iwasaki |
| 6,464,982 | B1 | 10/2002 | Lam |
| 6,471,860 | B1 | 10/2002 | Miltenyi et al. |
| 6,613,754 | B1 | 9/2003 | Wu |
| 7,135,183 | B1 | 11/2006 | Wang et al. |
| 7,323,176 | B2 | 1/2008 | Wang et al. |
| 2003/0068329 | A1 | 4/2003 | Kosuna et al. |
| 2003/0095981 | A1 | 5/2003 | Wong et al. |
| 2007/0104729 | A1 | 5/2007 | Wang et al. |
| 2007/0105814 | A1 | 5/2007 | Hua et al. |
| 2007/0231339 | A1 | 10/2007 | Yu et al. |
| 2008/0214442 | A1 | 9/2008 | Yu et al. |
| 2008/0247989 | A1 | 10/2008 | Shih et al. |

FOREIGN PATENT DOCUMENTS

| | | |
|---|---|---|
| WO | WO/2006/044616 | 4/2006 |
| WO | WO/2007/047021 | 4/2007 |
| WO | WO/2008/036421 | 3/2008 |

OTHER PUBLICATIONS

Blomberg K. et al., *Fluorescent europium chelates as target cell markers in the assessment of natural killer cell cytotoxicity*, J. Immunol. Methods, 1993, vol. 160, pp. 27-34.

Bowden, R. et al., *Alteration of Cytokine Levels in Murine Retrovirus Infection: Modulation by Combination Therapy*, International Journal of Immunopharmacology 1999, vol. 21, pp. 815-827.

Braciale T. et al., *Antigen presentation: structural themes and functional variations*, Immunology Today, 1991, vol. 12, No. 4, pp. 124-129.

Bronte V. et al., *IL-2 Enhances the Function of Recombinant Poxvirus-Based Vaccines in the Treatment of Established Pulmonary Metastases*, J. Immunol., 1995, vol. 154, pp. 5282-5292.

Chen H. et al., *Studies on the immuno-modulating and anti-tumor activities of Ganoderma lucidum (Reishi) polysaccharides*, Bioorg. Med. Chem., 2004, vol. 12, pp. 5595-5601.

Chen-Bettecken U. et al., *IgM RNA switch from membrane to secretory form is prevented by adding antireceptor antibody to bacterial lipopolysaccharide-stimulated murine primary B-cell cultures*, Proc. Natl. Acad. Sci., USA, 1985, vol. 82, pp. 7384-7388.

(Continued)

*Primary Examiner*—Christopher R Tate
*Assistant Examiner*—Randall Winston
(74) *Attorney, Agent, or Firm*—Eckman Basu LLP

(57) ABSTRACT

A method for treating an allergy by providing a pharmaceutical composition containing at least *Ganoderma lucidum* extract and administering a therapeutically effective amount of the composition to a patient in need thereof. Also disclosed is a method for treating an allergy by first purifying *Ganoderma lucidum* extract into at least one fraction, then providing a pharmaceutical composition comprising at least one of the *Ganoderma lucidum* fractions, and administering a therapeutically effective amount of the composition to a patient in need thereof. A method for alleviating symptoms of an allergy is disclosed. The symptoms of the allergy are alleviated by providing a pharmaceutical composition containing at least *Ganoderma lucidum* extract and administering an amount of the composition effective to decrease at least one of an IgE and IgG2a level, whereby the symptoms of the allergy are ameliorated.

6 Claims, 1 Drawing Sheet

OTHER PUBLICATIONS

Chien C., *Polysaccharides of Ganoderma lucidum alter cell immunophenotypic expression and enhance CD56⁻NK-cell cytotoxicity in cord blood*, Bioorg. Med. Chem., 2004, vol. 12, pp. 5603-5609.

Feltkamp M. et al., *Cytotoxic T lymphocytes raised against a subdominant epitope offered as a synthetic peptide eradicate human papillomavirus type 16-induced tumors*, Eur. J. Immunol., 1995, vol. 25, pp. 2638-2642.

Franz, G., *Polysaccharides in Pharmacy: Current Applications and Future Concepts*, Planta Medica, 1989, vol. 55, pp. 493-497.

Furusawa, E. et al., *Antitumor Activity of Ganoderma Lucidum, an Edible Mushroom, on Intraperitoneally Implanted Lewis Lung Carcinoma in Synergenic Mice*, Phytotherapy Research, vol. 6, 1992, pp. 300-304.

Grohmann U. et al, *$CD8^-$ cell activation to a major mastocytoma rejection antigen, P815AB: requirement for tumor helper peptides in priming for skin test reactivity to a P815AB-related peptide*, Eur. J. Immunol., 1995, vol. 25, pp. 2797-2802.

Halhoul M. et al., *Differential Determination of Glucose and Fructose, and Glucose- and Fructose-Yielding Substances with Anthrone*, Anal. Biochem., 1972, vol. 50, pp. 337-343.

Hellman M. et al., *Separation of Isomeric Polyphenyls by Adsorption Chromatography*, 1990, Analytical Chemistry, pp. 1206-1210.

Henderson R. et al., *Human Tumor Antigens are Ready to Fly*, Advances in Immunology, 1996, vol. 62, pp. 217-256.

Hsu H. et al.,*Extract of Reishi Polysaccharides Induces Cytokine Expression via TLR4-Modulated Protein Kinase Signaling Pathways*, J. Immunol., 2004, vol. 173, pp. 5989-5999.

Jermyn M., *Increasing the Sensitivity of the Anthrone Method for Carbohydrate*, Anal. Biochem., 1975, vol. 68, pp. 332-335.

Kim B. et al., *Antineoplastic Components of Korean Basidomycetes*, Korean Journal of Mycology, 1980, vol. 8, No. 2, pp. 107-114.

Kovacsovics-Bankowski M. et al.,*A Phagosome-to-Cytosol Pathway for Exogenous Antigens Presented on MHC Class I Molecules*, Science, 1995, vol. 267, pp. 243-246.

Lin K. et al., *Reishi Polysaccharides Induce Immunoglobulin Production through the TLR4/TLR2-mediated Induction of Transcription Factor Blimp-l*, J. Biol. Chem., 2006, vol. 281, No. 34, pp. 24111-24123.

Lo C. et al., *Simple fractionation of phospholipase $A_2$ analogues from snake venom by high-performance liquid chromatography*, J. Chromatogr. 1990, vol. 530, pp. 129-136.

Miyazaki, T. et al., *Structural Examination of an Alkali-Extracted, Water-Soluble Heteroglycan of the Fungus Ganoderma Lucidum*, Carbohydrate Research, 1982, vol. 109, pp. 290-294.

Mizuno et al., *Fractionation, Chemical Modification and Antitumor Activity of Water-insoluble Polysaccharides of the Fruiting Body of Ganoderma lucidum*, Journal of the Agricultural Chemical Society of Japan (Nippon Nôgeikagaku Kaishi), 1985, vol. 59, No. 11, pp. 1143-1151. [English language abstract enclosed].

Mosmann, T., *Rapid Colorimetric Assay for Cellular Growth and Survival: Application to Proliferation and Cytotoxicity Assays*, Journal of Immunological Methods, 1983, vol. 65, pp. 55-63.

Müller A. et al., *Receptor Binding and Internalization of a Water-Soluble (1→3)-β-D-Glucan Biologic Response Modifier in Two Monocyte/Macrophage Cell Lines*, J. Immunol., 1996, vol. 156, pp. 3418-3425.

Murphy, E. et al., *Detection of in vivo expression of interleukin-10 using a semi-quantitative polymerase chain reaction method in Schistosoma mansoni Infected Mice*, Journal of Immunological Methods, 1993, vol. 162, pp. 211-223.

Norkin L. et al., *Association of Caveolin with Chlamydia trachomatis Inclusions at Early and Late Stages of Infection*, Exp. Cell. Res., 2001, vol. 266, pp. 229-238.

Puccetti P. et al., *Use of a skin test assay to determine tumor-specific $CD8^-$ T cell reactivity*, Eur. J. Immuno., 1994, vol. 24, pp. 1446-1452.

Robbins P. et al., *A Mutated β-Catenin Gene Encodes a Melanoma-specific Antigen Recognized by Tumor Infiltrating Lymphocytes*, J. Exp. Med., 1996, vol. 183, pp. 1185-1192.

Sanchez, J. et al., *The mouse SWISS-2D PAGE database: a tool for proteomics study of diabetes and obesity*, Proteomics, 2001, vol. 1, pp. 136-163.

Shaffer A., *XBP1, Downstream of Blimp-I, Expands the Secretory Apparatus and Other Organelles, and Increases Protein Synthesis in Plasma Cell Differentiation*, Immunity, 2004, vol. 21, pp. 81-93.

Shao B. et al., *Immune receptors for polysaccharides from Ganoderma lucidum*, Biochem. Biophys. Res. Commun., 2004, vol. 323, pp. 133-141.

Shapiro-Shelef M. et al., *Blimp-1 Is Required for the Formation of Immunoglobulin Secreting Plasma Cells and Pre-Plasma Memory B Cells*, Immunity, 2003, vol. 19, pp. 607-620.

Shiao M. et al., *Natural Products and Biological Activities of the Chinese Medicinal Fungus Ganoderma lucidum*, American Chemical Society, 1994, pp. 342-354.

Sieckmann D. et al., *Activation of Mouse Lymphocytes by Anti-Immunoglobulin*, J. Exp. Med., 1978, vol. 147, pp. 814-829.

Smith J. et al., *Current Protocols in Molecular Biology*, John Wiley & Sons, Inc., 2005, Sec. 11.1-11.3.

Somani B. et al., *A Modified Anthrone-Sulfuric Acid Method for the Determination of Fructose in the Presence of Certain Proteins*, Anal. Biochem., 1987, vol. 167, p. 327-330.

Sone Y. et al. *Structures and Antitumor Activities of the Polysaccharides Isolated from Fruiting Body and the Growing Culture of Mycelium of Ganoderma lucidum*, Agric. Biol. Chem., 1985, vol. 49, pp. 2641-2653.

Spackman D. et al., *Automatic Recording Apparatus for Use in the Chromatography of Amino Acids*, Anal. Chem., 1958, vol. 30, pp. 1190-1206.

Usui, T. et al. *Isolation and characterization of antitumor active β-D-glucans from the fruit bodies of Ganoderma applanatum*, Carbohydrate Research, 1983, vol. 115, pp. 273-280.

Van Strijp J. et al., *Ligand Specificity of Purified Complement Receptor Type Three (CD11b/CD18, $\alpha m\beta 2, Mac-1$)*, J. Immunol., 1993, vol. 151, pp. 3324-3336.

Větvička V. et al., *Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells*, J. Clin. Invest., 1996, vol. 98, pp. 50-61.

Vitiello A. et al., *Development of a Lipopeptide-based Therapeutic Vaccine to Treat Chronic HBV Infection*, J. Clin. Inv. 1995, vol. 95, pp. 341-349.

Wang S. et al., *The Anti-Tumor Effect of Ganoderma Lucidum is Mediated by Cytokines Released from Activated Macrophages and T. Lymphocytes*, Int. J. Cancer, 1997, vol. 70, pp. 699-705.

Wang Y. et al., *Studies on the Immuno-Modulating and Antitumor Activities of Ganoderma lucidum (Reishi) Polysaccharides: Functional and Proteomic Analyses of a Fucose-Containing Glycoprotein Fraction Responsible for the Activities*, Bioorg. Med. Chem., 2002, vol. 10, pp. 1057-1062.

Widmann C. et al., *T helper epitopes enhance the cytotoxic response of mice immunized with MHC class I-restricted malaria peptides*, J. Immunol. Methods, 1992, vol. 155, pp. 95-99.

York I. et al., *Antigen Processing and Presentation by the Class I Major Histocompatibility Complex*, Annu. Rev. Immunol., 1996, vol. 14, pp. 369-396.

Zhang J. et al., *Activation of B lymphocytes by GLIS, a bioactive proteoglycan from Ganoderma lucidum*, Life Sci., 2002, vol. 71, pp. 623-638.

Asadullah, K. et al., *Interleukin-10 and Psoriasis*, Interleukin-10, 2006, pp. 161-168.

Raj, D. et al., *Keratinocyte Apoptosis in Epidermal Development and Disease*, J. Investigative Dermatology, 2006, vol. 126, pp. 243-257.

COMPOSITIONS AND METHODS FOR TREATING ALLERGIES, AUTO-IMMUNE DISEASES, AND IMPROVING SKIN CONDITION BY GANODERMA LUCIDUM (REISHI) POLYSACCHARIDES

RELATED APPLICATIONS

The present disclosure is incorporates by reference and claims the Paris Convention Priority of U.S. Provisional Application Ser. No. 60/969,119, filed Aug. 30, 2007, and entitled "Compositions and Methods for Treating Psoriasis by *Ganoderma Lucidum* (Reishi) Polysaccharides."

BACKGROUND

Allergies are hypersensitivity reactions to a previously encountered allergen. Allergens may be for instance pollen, dust, food, medication, and microorganisms. There are multiple ways an allergen can be introduced, including inhalation, ingestion, injection, and skin contact. Common allergic reactions include relatively milder symptoms, such as sneezing, itching, skin rashes, and running nose, and more severe symptoms, such as asthma and anaphylactic shock.

IgE plays an important role in allergies and allergic reactions. Upon introduction of an allergen, B cells of the individual produce large amounts of IgE. The IgE elicits an immune response by binding onto receptors found on leukocytes such as basophils and mast cells. When activated, these cells release chemical mediators such as histamine and cytokines that cause the characteristic symptoms of allergy.

IgG is an abundant immunoglobulin in humans that protects the individual from pathogens such as viruses, bacteria, and fungi. Upon introduction of a pathogen, IgG binds to the pathogen, allowing for various defense mechanisms such complement activation, opsonization for phagocytosis, and neutralization of pathogen toxins. IgG also plays a role in food allergies. In contrast to IgE-mediated allergic reactions to food, whose symptoms appear rapidly, IgG-mediated allergic reactions to food have a delayed onset. IgG can be divided into various subclasses based on their effector functions. The expression level of one subclass, IgG2a, represents Th1-associated responses in the immune system.

Auto-immune diseases are conditions in which a patient's body fails to recognize its own constituent parts as "self", resulting in an immune response against its own cells and tissues. Many different parts of the body can be affected by auto-immune diseases, including nerves, tissues, organs, and muscles.

SUMMARY

According to one aspect of the present disclosure, a method is disclosed for treating an allergy. The method comprises the steps of providing a pharmaceutical composition containing at least *Ganoderma lucidum* extract and administering a therapeutically effective amount of the composition to a patient in need thereof.

A method is disclosed for treating an auto-immune disease. The method comprises the steps of providing a pharmaceutical composition containing at least *Ganoderma lucidum* extract and administering a therapeutically effective amount of the composition to a patient in need thereof.

A method is disclosed for treating blemished skin and improving skin condition. The method comprises the steps of providing a pharmaceutical composition containing at least *Ganoderma lucidum* extract and administering a therapeutically effective amount of the composition to a patient in need thereof.

According to another aspect of the present disclosure, a method is disclosed for treating an allergy. The method comprises the steps of first purifying *Ganoderma lucidum* extract into at least one fraction, then providing a pharmaceutical composition comprising at least one of the *Ganoderma lucidum* fractions, and administering a therapeutically effective amount of the composition to a patient in need thereof.

A method is disclosed for treating an auto-immune disease. The method comprises the steps of first purifying *Ganoderma lucidum* extract into at least one fraction, then providing a pharmaceutical composition comprising at least one of the *Ganoderma lucidum* fractions, and administering a therapeutically effective amount of the composition to a patient in need thereof.

A method is disclosed for treating blemished skin and improving skin condition. The method comprises the steps of first purifying *Ganoderma lucidum* extract into at least one fraction, then providing a pharmaceutical composition comprising at least one of the *Ganoderma lucidum* fractions, and administering a therapeutically effective amount of the composition to a patient in need thereof.

According to the another disclosure, a pharmaceutical composition for treating an allergy is disclosed. The pharmaceutical composition comprises a *Ganoderma lucidum* extract.

A pharmaceutical composition for treating an auto-immune disease is disclosed. The pharmaceutical composition comprises a *Ganoderma lucidum* extract.

A pharmaceutical composition for treating blemished skin and improving skin condition is disclosed. The pharmaceutical composition comprises a *Ganoderma lucidum* extract.

According to another aspect of the present disclosure, a method for alleviating symptoms of an allergy is disclosed. The method comprises the steps of providing a pharmaceutical composition containing at least *Ganoderma lucidum* extract and administering an amount of the composition effective to decrease at least one of an IgE and IgG2a level, whereby the symptoms of the allergy are ameliorated.

A method for alleviating symptoms of an auto-immune disease is disclosed. The method comprises the steps of providing a pharmaceutical composition containing at least *Ganoderma lucidum* extract and administering an amount of the composition effective to ameliorate the symptoms of the auto-immune disease.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
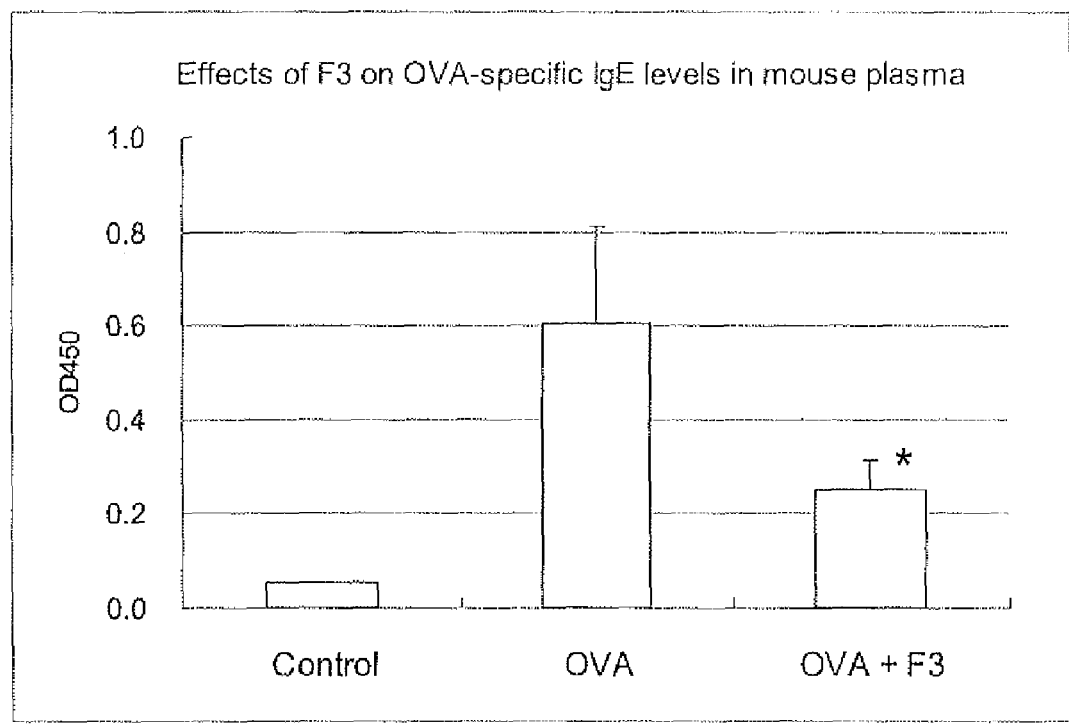
FIG. 1 is a bar graph showing the effect of F3 on OVA-specific IgE levels in plasma.

The present disclosure relates to pharmaceutical compositions containing *Ganoderma lucidum* extract to treat allergies, auto-immune diseases, and skin disorders and damages. The methods and compositions address treatment of allergies as well as treatment of diseases, disorders, symptoms, immune reactions and responses often characterized with inflammation. The methods and compositions also address treatment of damaged, blemished, and aged skin, as well as improvement of skin conditions.

The phrase "Ganoderma lucidum" refers to the Ganoderma lucidum fungus, which also includes any tissue, part or fraction therefrom and/or any preparation thereof including homogenates, suspension, filtrates, filtration residues and solution. Other names for Ganoderma lucidum include Reishi and Ling-Zhi.

The term "extract" refers to any solid, viscid, and liquid substance obtained through extraction from a given substance. In the present disclosure, a Ganoderma lucidum extract includes any solid, viscid, and liquid substance extracted from Ganoderma lucidum plant tissue.

Various methods and procedures for extraction are known and used by those skilled in the art. Such methods and procedures include both physical and chemical processes, including solvent utilization, distillation, percolation, and supercritical fluid extraction. The extract may be further filtered or concentrated as desired. In one example, a Ganoderma lucidum extract is obtained by treating homogenized Ganoderma lucidum plant tissue with 0.1 N NaOH for a predetermined time.

According to exemplary implementations, the pharmaceutical composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the extract. Excipients, adjuvants and other ingredients may also be included in the composition. The pharmaceutical composition may also be incorporated in cosmetics and skin care products that are applied topically.

The composition should be stable during manufacture and storage. The Ganoderma lucidum extract or specific constituents of the extract may be encapsulated, with agents such as aluminum monostearate, gelatin, and biodegradable and biocompatible polymers, to prevent undesired degradation in the body or by other ingredients in the composition. Anti-bacteria and anti-fungal agents such as benzyl alcohols, parabens, chlorobutanol, phenol, ascorbic acid, and thimerosal may also be included in the composition.

According to the present disclosure, a pharmaceutical composition containing Ganoderma lucidum extract for treating an allergy is disclosed. In exemplary implementations, the Ganoderma lucidum extract decreases IgE and/or IgG2 a levels. The decrease in IgE and/or IgG2a levels plays a role in the abatement of allergies, allergic reactions, and symptoms of allergies.

Other diseases, disorders, and inflammatory symptoms associated with increased IgE levels may also be treated with the composition containing Ganoderma lucidum extract. Examples include but are not limited to asthma, eczema, and atopy.

The Ganoderma lucidum extract may also induce increased IL-10 and/or IL-1Ra expression. In exemplary implementations, the increased expression of IL-10 and IL-1Ra plays a role in the abatement of allergies, allergic reactions, and symptoms of allergies. Inflammatory responses may be alleviated with increased IL-10 and/or IL-1Ra expression.

Other diseases and inflammatory symptoms associated with decreased IL-10 and/or IL-1Ra expression may also be treated with the composition containing Ganoderma lucidum extract. Examples include but are not limited to arthritis, inflammatory bowel diseases, multiple sclerosis and inflammation due to transplantation or viral infections.

A pharmaceutical composition containing Ganoderma lucidum extract for treating an auto-immune disease is disclosed. In exemplary implementations, the auto-immune disease is characterized with inflammation. Such auto-immune diseases include acute disseminated encephalomyelitis (ADEM), ankylosing spondylitis (AS), coeliac diseases, Crohn's disease, Guillain-Barre syndrome (GBS), Hashimoto's disease, optic neuritis, Ord's thyroiditis, rheumatoid arthritis, and temporal arteritis. In an exemplary implementation, the pharmaceutical composition is used to treat systemic lupus erythematosus (i.e. lupus).

A pharmaceutical composition containing Ganoderma lucidum extract for treating blemished skin and improving skin condition is disclosed. Blemished skin includes all imperfections of the skin that may have been caused by factors such as aging, acne, diet, infection, trauma, disease, disorders, medication, solar and electromagnetic radiation. In exemplary implementations, the pharmaceutical composition can be used to treat skin damages, such as wrinkles, scars, and spots, and skin disorders, such as dermatitis and erythema. The pharmaceutical composition may also be used to promote healthier skin and improve skin appearance.

In some exemplary implementations, the pharmaceutical composition can be used in conjunction with skin care products for enhanced treatment, restoration, maintenance, and protection of skin. The skin care products, for instance lotions, moisturizers, and creams, are applied topically while the pharmaceutical composition may be taken orally.

In one aspect of the present disclosure, a method is provided for treating an allergy. The method comprises the steps of providing a pharmaceutical composition containing at least Ganoderma lucidum extract and administering a therapeutically effective amount of the composition to a patient in need thereof.

A method is provided for treating an auto-immune disease. The method comprises the steps of providing a pharmaceutical composition containing at least Ganoderma lucidum extract and administering a therapeutically effective amount of the composition to a patient in need thereof.

A method is provided for treating blemished skin and improving skin condition. The method comprises the steps of providing a pharmaceutical composition containing at least Ganoderma lucidum extract and administering a therapeutically effective amount of the composition to a patient in need thereof.

Administration of the composition may be achieved through various methods to different parts of the body, including intravenous, intradermal, subcutaneous, oral (e.g., inhalation), transdermal (i.e., topical), transmucosal, and rectal administration.

Topical administration to a localized area of skin may be achieved with compositions include creams, gels, ointments, and salves. Polyethylene glycols, propylene glycols, glycerin, and other synthetic solvents may be used in the compositions.

In other exemplary implementations, the composition is a solution or suspension injected parenterally, intradermally, or subcutaneously. Carriers include water, saline solutions, and other synthetic solvents. Buffers such as acetates, citrates, and phosphates may be used, as well agents for adjusting tonicity, such as sodium chloride and dextrose, and agents for adjusting pH, such as hydrochloric acid and sodium hydroxide.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

In another aspect of the present disclosure, a method is provided for treating an allergy. The method comprises the steps of filtering Ganoderma lucidum extract into at least one fraction, providing a pharmaceutical composition having at least one of the Ganoderma lucidum fractions, and administering a therapeutically effective amount of the composition to a patient in need thereof.

A method is provided for treating an auto-immune disease. The method comprises the steps of filtering Ganoderma lucidum extract into at least one fraction, providing a pharmaceutical composition having at least one of the Ganoderma lucidum fractions, and administering a therapeutically effective amount of the composition to a patient in need thereof.

A method is provided for treating blemished skin and improving skin condition. The method comprises the steps of filtering Ganoderma lucidum extract into at least one fraction, providing a pharmaceutical composition having at least one of the Ganoderma lucidum fractions, and administering a therapeutically effective amount of the composition to a patient in need thereof.

The term "fraction" refers to one of the separable constituents of a substance. The fractions are collected based on differences in a specific property of the individual constituents. In exemplary implementations, the fractions are identified by their respective abilities to absorb light.

The term "filtering" refers to any procedure used to separate a constituent of a substance from other constituents of the substance. Various methods and procedures for filtration are known and used by those skilled in the art. Such methods and procedures include dialysis and gel filtration chromatography. In one example, Ganoderma lucidum extract is filtered using a Sephaceryl S-500 column and eluting with a Tris buffer solution to form one or more fractions.

In at least one exemplary implementation of the present disclosure, the Ganoderma lucidum fraction, herein referred to as "F3" or "Fraction 3", contains a glycoprotein with fucose residues. In various exemplary implementations, the fucose residues are bound with α-1,2-fucosidic linkages or α-3,4-fucosidic linkages, and may be located terminally, in a region proximate to a free end of a chain of sugars. In further exemplary implementations, the fucose-containing glycoprotein can also comprise of glucose, mannose, N-acetylglucosamine, xylose, and galactose. An amino acid component may also be included, and may comprise modifications that do not adversely alter characteristics of the fucose-containing glycoprotein.

In another aspect of the present disclosure, a method is provided for alleviating symptoms of an allergy. The method comprises the steps of providing a pharmaceutical composition containing at least Ganoderma lucidum extract and administering an amount of the composition effective to decrease at least one of an IgE and IgG2a level, whereby the symptoms of the allergy are ameliorated.

A method is provided for alleviating symptoms of an auto-immune disease. The method comprises the steps of providing a pharmaceutical composition containing at least Ganoderma lucidum extract and administering an amount of the composition effective to ameliorate the symptoms of the auto-immune disease.

EXAMPLE

A more complete understanding of the present disclosure can be obtained by reference to the following specific examples and figures. The examples and figures are described solely for purposes of illustration and are not intended to limit the scope of the disclosure. Changes in form and substitution of equivalents are contemplated as circumstances may suggest or render expedient. Although specific terms have been employed herein, such terms are intended in a descriptive sense and not for purposes of limitations. Modifications and variations of the disclosure as hereinbefore set forth can be made without departing from the spirit and scope thereof, and, therefore, only such limitations should be imposed as are indicated by the appended claims.

Treatment of Allergies: Effects of F3 on OVA-Specific IgE and IgG2a Levels in Plasma.

Figure 2:
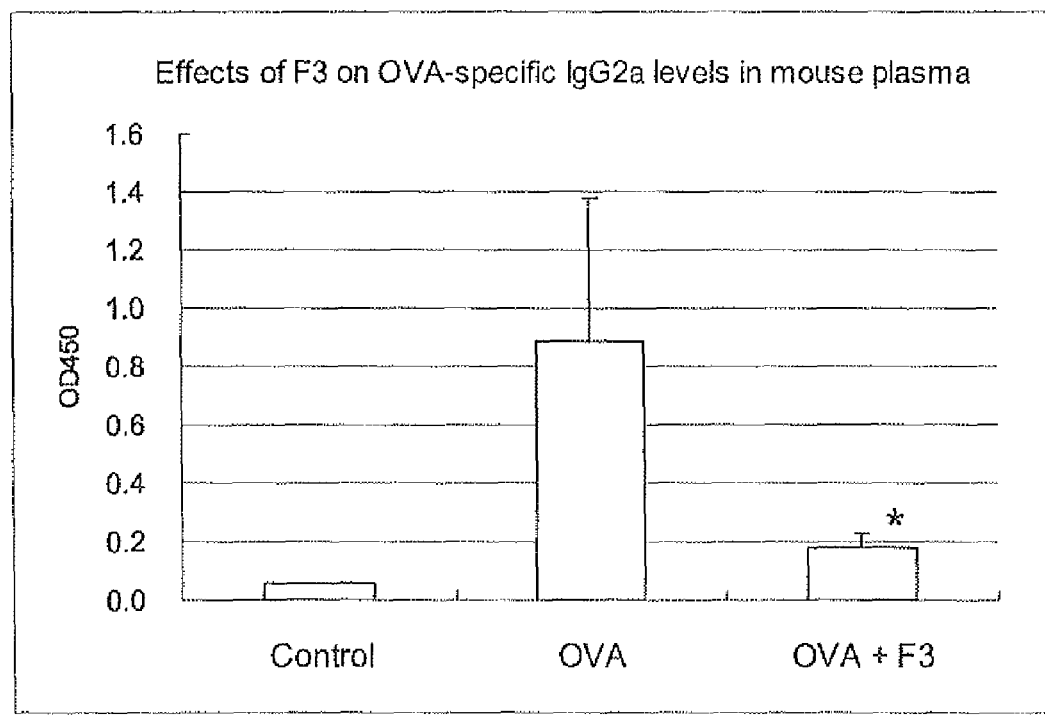
FIG. 2 is a bar graph showing the effect of F3 on OVA-specific IgG2a levels in plasma.

Chicken egg albumin grade III—aluminum hydroxide gel (OVA) was used to induce allergy. BALB/c mice were sensitized and challenged with alum-precipitated antigen (OVA/alum) on days 7, 14 and 21 by intraperitoneal injection (i.p.) of 0.5 ml OVA/alum solution containing 8 μg of OVA and 2 mg Al(OH)$_3$ to induce primary immunity. Non-sensitized control mice received alum only. On day 30, 31, and 32 mice were challenged with OVA (80 μl/20 g mouse; 5 mg/kg) intranasally once per day. Plasma was obtained at 24 h after last OVA challenge. OVA-specific IgE and IgG2a levels were determined by ELISA. FIGS. 1 and 2 illustrate the results of the experiment. FIG. 1 is a bar graph showing the effect of F3 on OVA-specific IgE levels in plasma. FIG. 2 is a bar graph showing the effect of F3 on OVA-specific IgG2a levels in plasma. Data represent mean±SD (n=5). The study groups include phosphate buffered saline (PBS) challenge (Control), OVA challenged (OVA) and OVA challenged+daily F3 intraperitoneal treatment (660 mg/kg, day 0 to 30) (OVA+F3). OVA+F3 showed a $P<0.05$ compared to non-F3-treated OVA-challenge mice (OVA) for both IgE and IgG2a expression levels.

While the method and agent have been described in terms of what are presently considered to be the most practical and preferred implementations, it is to be understood that the disclosure need not be limited to the disclosed exemplary implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A method for treating an allergy, the method comprising:
   providing a pharmaceutical composition comprising a sodium hydroxide extract solution of Ganoderma lucidum; and
   administering a therapeutically effective amount of the composition to a patient in need thereof.

2. The method of claim 1 wherein said composition is administered intravenously, intradermally, subcutaneously, orally, transdermally, transmucosally, or rectally.

3. The method of claim 1 wherein said composition is formulated as a cream, gel, salve, ointment, solution, tablet, capsule, spray, or patch.

4. The method of claim 1 wherein the administration of said *Ganoderma lucidum* extract decreases IgE levels in the patient.

5. A method for alleviating symptoms of an allergy, the method comprising:

providing a pharmaceutical composition comprising a sodium hydroxide extract solution of *Ganoderma lucidum*; and administering an amount of the composition effective to decrease at least one of an IgE and IgG2a level, whereby the symptoms of the allergy are ameliorated.

6. The method of claim 1, wherein the composition is administered in an amount sufficient for inducing an increase in at least one of IL-10 and IL-1Ra expression.

* * * * *